United States Patent
Epner et al.

(10) Patent No.: US 10,350,253 B2
(45) Date of Patent: Jul. 16, 2019

(54) USE OF AMERICAN GINSENG TO COUNTERACT CANNABIS-INDUCED INTOXICATION

(71) Applicant: ENGEN MEDICAL CORPORATION, San Diego, CA (US)

(72) Inventors: Paul Epner, San Diego, CA (US); Richard Zimmer, III, Mandeville, LA (US); Bill W. Massey, Heber Springs, AR (US)

(73) Assignee: ENGEN MEDICAL CORPORATION, San Diego, CA (US)

( * ) Notice: Subject to any disclaimer, the term of this patent is extended or adjusted under 35 U.S.C. 154(b) by 13 days.

(21) Appl. No.: 15/863,266

(22) Filed: Jan. 5, 2018

(65) Prior Publication Data

US 2018/0193395 A1    Jul. 12, 2018

Related U.S. Application Data

(60) Provisional application No. 62/443,067, filed on Jan. 6, 2017.

(51) Int. Cl.
| | | |
|---|---|---|
| *A61K 36/00* | (2006.01) | |
| *A61K 36/258* | (2006.01) | |
| *A23L 33/105* | (2016.01) | |
| *A23G 4/06* | (2006.01) | |
| *A23G 4/08* | (2006.01) | |
| *A61K 9/68* | (2006.01) | |
| *A61K 9/20* | (2006.01) | |
| *A61P 25/00* | (2006.01) | |

(52) U.S. Cl.
CPC .............. *A61K 36/258* (2013.01); *A23G 4/06* (2013.01); *A23G 4/068* (2013.01); *A23G 4/08* (2013.01); *A23L 33/105* (2016.08); *A61K 9/0058* (2013.01); *A61K 9/2018* (2013.01); *A61P 25/00* (2018.01); *A23V 2002/00* (2013.01); *A61K 9/2009* (2013.01)

(58) Field of Classification Search
CPC ..................................................... A61K 36/00
USPC ......................................................... 424/725
See application file for complete search history.

(56) References Cited

U.S. PATENT DOCUMENTS 9,572,364 B2 *   2/2017   Langan .................... A23L 27/86

* cited by examiner

*Primary Examiner* — Michael V Meller
(74) *Attorney, Agent, or Firm* — Juan J. Lizarraga

(57) ABSTRACT

A composition and method for the use of *Panax quinquefolius* for the attenuation of *Cannabis*-induced dysphoria where dosage can be effectively administered in a gum base cold pressed into a tablet containing at least 300 mg of *Panax quinquefolius* and Maltitol, Sorbitol, Isomalt, Xylitol, natural & artificial flavors, vegetarian magnesium stearate, Sucralose and Silicon dioxide.

1 Claim, No Drawings

USE OF AMERICAN GINSENG TO COUNTERACT CANNABIS-INDUCED INTOXICATION

This application claims priority from U.S. Provisional Application No. 62/433,067 (the '067 application), filed Jan. 6, 2017. The '067 application is incorporated herein by reference.

BACKGROUND OF THE INVENTION

*Cannabis* (aka marijuana) is a genus of flowering plants that consists of three subspecies, *Cannabis sativa, Cannabis indica,* and *Cannabis ruderalis. Cannabis* produces hundreds of cannabinoids, which are terpeno-phenolic compounds. Some of these cannabinoids produce psychoactive effects (e.g. delta-9-tertrahydrocannabinol) whereas other cannabinoids are biologically-active and produce wide-ranging effects as disparate as conjunctive vasodilation, immune system regulation, stimulation of appetite, sleep-induction, and analgesia. Medical use of *Cannabis* is practiced today and has a history going back thousands of years, however, the medical utility of *Cannabis* is a topic of much contention. Several states have legalized the recreational and medical use of *Cannabis* and more states have placed *Cannabis* legalization on ballots for the voters of these states to determine its legal status. Currently, the US Federal government does not recognize the medical utility of *Cannabis* but has not interceded in the sale and distribution of *Cannabis* in those states where its use has been legalized. The eventual legal status of *Cannabis* at the federal level is uncertain. Despite the confusing and evolving legal status of *Cannabis*, it is one of the most commonly-used psychoactive substances in the world, exceeded only by ethanol-containing beverages, tobacco (nicotine), and coffee (caffeine).

One of the known biological effects of the consumption of *Cannabis* is intoxication via psychoactive cannabinoids (e.g. delta-9-tetrahydrocannabinol). The psychoactive effects of *cannabis* are the reason it is used as a recreational intoxicant. The mechanism for *Cannabis*-induced intoxication is via agonism of cannabinoid subtype 1 (CB1) receptors. While the intoxication from *cannabis* is usually described as pleasurable, high doses of *cannabis* can result in dysphoria, including panic, generalized anxiety, and adverse bodily sensations. The lack of quality control and great differences in cannabinoid content between *cannabis* strains can result in some *cannabis* extracts to be extremely potent, and more likely to induce high-dose *cannabis*-induced dysphoria. This risk is increased when the *cannabis* is ingested as an edible form (e.g. *cannabis*-infused brownies, cookies, and lozenges). It is proposed that these dysphoric effects of high-dose *cannabis* would be reversed by chemical antagonists or inverse agonists of the CB1 receptor.

SUMMARY OF THE INVENTION

It is an object of this invention to provide a composition of *Panax quinquefolius* comprising a dosage in an amount effective for the attenuation of *Cannabis*-induced dysphoria.

It is a further object of this invention to provide the composition of *Panax quinquefolius* within a gum base for efficacious delivery to the user through the ordinary process of gum chewing, where the gum base further comprises Maltitol, Sorbitol, Isomalt, Xylitol and other components.

It is a further object of this invention to provide a method for detoxification comprising administering a therapeutically effective amount of a composition containing American Ginseng that reduces the psychotropic activity caused by the consumption of *cannabis*.

DETAILED DESCRIPTION OF THE INVENTION

The present invention described herein is the use of *Panax quinquefolius* (aka American Ginseng), including any processed (e.g. extracts, conjugates, heated, cooked, etc.) or unprocessed form of the plant, including roots, leaves and seeds, for the attenuation of *Cannabis*-induced dysphoria incorporated within a gum base with the below included ingredients for efficacious delivery to the user through the ordinary process of gum chewing. The gum base is formulated utilizing a cold pressed manufacturing process to incorporate all of the ingredients with heightened efficacy into a circular half inch diameter tablet. The ingredients incorporated into the gumbase are, Maltitol, Sorbitol, Isomalt, Xylitol, American Ginseng (African *Panax quinquefolius*) 300 mg per piece, natural & artificial flavors, vegetarian magnesium stearate, Sucralose and Silicon dioxide.

*Panax quinquefolius* is a herbaceous perennial plant in the ivy family, commonly used as herbal medicine. American ginseng was formerly particularly widespread in the forested regions of the Eastern United States, Appalachian and Ozark regions. However, due to its popularity and destruction of its habitat, the wild plant has been overharvested, and is rare in most parts of the United States and Canada. Currently, most American ginseng is grown commercially and is not wild-harvested. American ginseng is used for a wide variety of ailments in herbal medicine, from improving digestion, to improving immune function, to treating insomnia and anxiety. Approximately 200 substances have been isolated from ginseng including ginsenosides, polyacetylenes, alkaloids, polysaccharides, oligosaccharides, oligopeptides, phenolic compounds, lipids, vitamins, and minerals (Kolodziej et al., Chemical composition and chosen bioactive properties of *Panax quinquefolius* extracts. Chemija 24(2):151-159, 2013). Nonvolatile ginsenosides and falcarinol, a natural pesticide and fatty alcohol, are believed to be the main pharmacologically-active ginseng constituents (Kolodziej et al., Chemical composition and chosen bioactive properties of *Panax quinquefolius* extracts. Chemija 24(2):151-159, 2013).

Of special interest to *cannabis*-induced dysphoria, is the presence of falcarinol in American ginseng. Falcarinol is found at concentrations of up to 14% in the roots of *Panax quinquefolius* (Kolodziej et al., Chemical composition and chosen bioactive properties of *Panax quinquefolius* extracts. Chemija 24(2):151-159, 2013). Falcarinol contains special properties with regard to reducing the psychoactive effects of *cannabis*. Most importantly, falcarinol has been shown to be a potent inverse agonist at the CB1 receptor, and thus would reverse the effects of CB1 agonism, and thereby attenuate *cannabis*-induced dysphoria (Leonti et al., Falcarinol is a covalent cannabinoid CB1 receptor antagonist and induces pro-allergic effects in skin. Biochemical Pharmacology 79(12):1815-1826, 2010). American ginseng, via Falcarinol's CB1 inverse agonist properties, would thereby attenuate *cannabis*-induced dysphoria.

It is an object of this invention to provide a method for detoxification comprising administering a therapeutically effective amount of a composition containing American Ginseng that reduces the psychotropic activity caused by the consumption of *cannabis*.

What is claimed is:

1. A method to reverse the intoxication in a human intoxicated by *cannabis* use consisting essentially of administering to said human a therapeutically effective amount of a composition of *Panax quinquefolius* where the amount of *Panax quinquefolius* is at least 300 mg in the composition and the composition is a chewing gum.

* * * * *